United States Patent [19]
Hairston et al.

[11] Patent Number: 5,999,250
[45] Date of Patent: Dec. 7, 1999

[54] SYSTEM FOR DETECTING FLUORESCING COMPONENTS IN AEROSOLS

[75] Inventors: Peter P. Hairston, St. Paul; Frederick R. Quant, Shoreview, both of Minn.

[73] Assignee: TSI Corporation, St. Paul, Minn.

[21] Appl. No.: 09/042,921

[22] Filed: Mar. 17, 1998

Related U.S. Application Data

[60] Provisional application No. 60/040,852, Mar. 17, 1997.

[51] Int. Cl.$^6$ ............................ G01N 21/64; G01N 15/02
[52] U.S. Cl. ...................... 356/73; 250/461.2; 356/318; 356/336
[58] Field of Search ................................. 356/72, 73, 317, 356/318, 336; 280/458.1, 459.1, 461.1, 461.2

[56] References Cited

U.S. PATENT DOCUMENTS

| | | | |
|---|---|---|---|
| 3,946,239 | 3/1976 | Salzman et al. | 250/461.2 |
| 4,341,993 | 7/1982 | Brunsting et al. | 250/458.1 |
| 4,943,159 | 7/1990 | Oetliker et al. | 356/73 |
| 5,110,204 | 5/1992 | Miles et al. | 356/28 |
| 5,127,729 | 7/1992 | Oetliker et al. | 359/317 |
| 5,681,752 | 10/1997 | Prather | 436/173 |
| 5,701,012 | 12/1997 | Ho | 250/461.2 |
| 5,721,613 | 2/1998 | Linowski et al. | 356/318 |

OTHER PUBLICATIONS

Single Particle Detector Method and Apparatus Using Light Scattering Technique; 3308.7–US–01.

*Primary Examiner*—F. L. Evans
*Attorney, Agent, or Firm*—Frederick W. Niebuhr

[57] ABSTRACT

An electro-optical aerosol characterizing system includes a continuous wave laser for generating two beams in the red wavelength range, intersecting a particle stream at slightly spaced apart locations. A pulsed UV laser generates a beam that intersects the particle stream at a third location downstream. Laser energy scattered by each particle as it passes the first two locations, is used to compute aerodynamic sizes and UV laser pulsing times, so that in each case the UV beam irradiates the particle at the downstream location. Particles containing biological materials or other fluorescing components emit fluorescence signals in response to the irradiation. Accordingly, the system provides information about particle composition as well as particle size.

40 Claims, 3 Drawing Sheets

SYSTEM FOR DETECTING FLUORESCING COMPONENTS IN AEROSOLS

This application claims the benefit of Provisional patent application Ser. No. 60/040,852 entitled "Method for Triggering a Pulsed Light Source to Irradiate Individual Particles Undergoing Acceleration", filed Mar. 17, 1997.

BACKGROUND OF THE INVENTION

The present invention relates to instruments and processes for analyzing aerosol particles, and more particularly to apparatus for characterizing the particles as to their size and the presence of biological components.

Aerosols composed of biological particles comprise a small fraction of the aerosols present in our atmosphere. Nonetheless, there is an increasing interest in analyzing biological aerosols, which can incorporate bacteria, fungi and pollens. Certain diseases, for example, tuberculosis, influenza and pneumonia, are transmitted via airborne particles or droplets. Diseases that affect livestock and other farm animals, (e.g. anthrax and brucellosis) and diseases that affect crops, likewise are transmitted through the air. Airborne pollens cause allergic reactions in humans. The Persian Gulf War, and recent news reports about individuals in possession of anthrax, have galvanized public concerns over biological warfare and the potential for terroristic release of airborne biological contaminants. The study of airborne fungi, pollen and other components is now recognized as a key concern in the control of indoor environments, e.g. office buildings. Thus, it is not surprising to see the study of biological aerosols playing an increasing role in such diverse areas as epidemiology and other medical fields, agriculture, building management and defense.

A variety of devices have been used to detect and identify airborne biological particles, e.g. pollen traps, impingers, impactors, and cyclones that collect particles for subsequent identification. These methods fail to deliver real time results, and are time consuming and labor intensive, particularly in cases that require growing bacteria.

Similarly, a variety of particle sizing methods and systems are known. For example, U.S. Pat. No. 5,561,515 (Hairston, et al), assigned to the assignee of the present application, discloses an instrument for measuring the aerodynamic size of particles in the micron and submicron ranges. Particles in series are accelerated through a nozzle, and upon exiting the nozzle encounter two relatively long wavelength (red or infrared) laser beams. Aerodynamic size is determined based on a time-of-flight measurement, i.e. the transit time of each particle from the first beam to the next. Transit time is measured by detecting light scattered by the particle as it travels through both beams. A partial overlapping of the beams is used advantageously to reject any erroneous readings from single-trigger or coincidence events.

It has been found that biological cells contain fluorescent molecules, e.g. flavins, amino acids and nicotinamide adenine nucleotides, and thus emit fluorescent signals when exposed to excitation energy within a range of excitation frequencies. With this in mind, U.S. Pat. No. 5,701,012 (Ho) discloses a device for determining aerodynamic sizes, and subjecting the particles in sequence to ultraviolet laser light, then detecting any fluorescence. The ultraviolet laser is operated in the CW (continuous wave) mode, so that excitation occurs as particles reach that part of the particle path intersected by the UV laser. A similar technique is discussed in an article by Pinnick et al entitled "Fluorescence Particle Counter for Detecting Airborne Bacteria and Other Biological Particles", *Aerosol Science and Technology*, Volume 23, pp. 653–664 (1995). The continuous application of laser energy avoids the need to time individual particles for timing a pulsed UV laser. At the same time, it is difficult to maintain continuous lasers at the high power levels necessary to achieve the particle irradiation energy needed to trigger readily detectable fluorescent emissions. Moreover, continuous lasers maintained at any power are inefficient in this application, given that the system requires only intermittent irradiation.

Another approach, disclosed in U.S. Pat. No. 5,681,752 (Prather), involves determining aerodynamic size and chemical composition of particles. A stream of particles is drawn through a vacuum device with several stages separated by skimmers. Each particle is accelerated to a speed inversely related to its aerodynamic size, then remains substantially at that speed as it moves through two spaced apart beams. The travel time from one beam to the next yields a timing signal used to fire a high intensity laser downstream of the velocity measuring beams. The high intensity laser desorbs the particles and ionizes their molecule. The ions are then subjected to mass spectrometry.

Although measuring the particles at constant velocities affords relative simplicity in timing the downstream laser, the constant velocities are attainable only in a near vacuum (typically $10^{-6}$ to $10^{-7}$ torr), which requires high powered vacuum pump and inlet skimmers. A high intensity laser is required to free molecular ions from the particles. The mass spectrometry stage requires significant additional hardware for post irradiation analysis, including electrically charged ion accelerating plates, a flight tube for ion separation, and an ion detector. The travel of ions through the flight tube takes on the order of hundreds of microseconds, and thus limits the rate at which particles can be measured.

Therefore, it is an object of the present invention to provide a system capable of generating real time information about particle size and composition, using a relatively low power, pulsed laser or other source of excitation energy.

Another object is to provide an aerosol analysis system in which time-of-flight measurements, taken individually during particle accelerations are rapidly converted into timing information used to intermittently generate excitation energy.

A further object is to provide, in a system for generating aerodynamic size information based on scattered light and particle composition information based on induced particle emissions, a detecting arrangement with improved sensitivity to scattered light and emitted signals.

Yet another object is to provide a process that combines relatively low energy lasers for time-of-flight measurements and excitation of particles with fluorescent components, with enhanced sensitivity for detecting scattered and emitted energy, to generate more reliable real time particle size and composition information.

SUMMARY OF THE INVENTION

To achieve these and other objects, there is provided a process for characterizing particles in aerosols, including:

a. causing an aerosol to move along a predetermined path as a stream of successive particles detectable individually at least at first and second different locations along the path;

b. accelerating the aerosol along the predetermined segment of the path that includes the first and second locations;

c. measuring respective transit times for the particles, with the transit time in each case indicating the time for the respective particle to travel from the first location to the second location;

d. intermittently causing excitation energy to intercept the path at a third location downstream from the first and second locations, to individually irradiate each of the particles with the excitation energy, wherein the excitation energy has a frequency within a range selected to trigger a responsive emission by a predetermined constituent; and e. responsive to each episode of said irradiating, sensing for the presence of a responsive emission from the particle to facilitate determining whether that particle contains the predetermined constituent.

In cases where the predetermined constituent is biological or otherwise fluorescing, the excitation frequency is selected for its capacity to induce fluorescence. Preferably, the particles are measured by directing first and second coherent energy beams across the path at separate first and second locations, then detecting coherent energy scattered by each particle as it intersects each beam. The transit time can be used to indicate aerodynamic size. The intensity of the scattered energy can be measured as a further indication of particle size. The preferred device for the intermittent generation of excitation energy is by a pulsed laser. The wavelengths most useful for fluorescence excitation, i.e. ultraviolet light in the range of about 200 to 400 nm, are more easily generated using pulsed lasers. As compared to continuous lasers, pulsed lasers are smaller, more rugged, more efficient, and produce less excess heat. The laser can be pulsed in response to sensing coherent energy scattered by each particle as the particle passes at least one of the first and second locations. More preferably, the laser is pulsed in response to a transit time based on sensing the particle as it passes both locations. The time to generate the excitation energy is determined rapidly, based on a look-up table containing multiple time delay values, each individually associated with one of multiple transit times stored as addresses. Accordingly, a transit time input to the table leads to virtually instantaneous generation of the associated time delay value as an output of the table, for use in timing the excitation energy to irradiate the particle. A similar look-up table can be used for rapid generation of aerodynamic size values.

The responsive emissions from each particle, typically fluorescence signals, tend to be weak and can be difficult to extinguish from noise. Accordingly, a device to concentrate the responsive emission energy provides enhanced sensitivity. More particularly, an ellipsoidal mirror is positioned near the third location, with one of its two foci at the third location. The detector, typically a fluorescence detector, is positioned at the other one of the foci. As a result, energy emanating from the third location, despite reaching the ellipsoidal mirror at a variety of locations, is reflected toward the other focus, i.e. toward the detector. A similar positioning of a second ellipsoidal reflector can reduce the power requirements for the coherent energy lasers used in determining aerodynamic size.

Further in accordance with the present invention, there is provided a particle characterizing system including a flow generating device for moving an aerosol along a designated path with particles of the aerosol in series. The flow generating device accelerates the aerosol along a selected segment of the path including first and second different locations along the path. A measuring device is provided for measuring respective transit times, indicating for each one of the particles a time required for the particle to travel from the first location to the second location. An excitation component is provided for generating excitation energy at a frequency within a predetermined excitation frequency range, selected to cause an emission by a particle in response to irradiation by the excitation energy. The excitation component causes the excitation energy to intersect the path at a third location downstream of the first and second locations. A timing component causes the excitation component to generate the excitation energy intermittently as different ones of the particles travel past the third location, thereby to irradiate each of the particles with the excitation energy. A sensing component is used to detect any emission by the particle responsive to the irradiation.

The excitation component preferably includes a pulsed UV laser—operated to generate coherent energy having a wavelength in the range of about 349–355 nm. In response to this irradiation, biological components in the particles emit fluorescent signals, generally at a longer wavelength than that of the excitation energy, i.e. in the range of 400–580 nm.

According to a further aspect of the invention, several detectors can be positioned to sense different frequencies or frequency ranges of radiation emitted by the particles, permitting an indication of particle composition with respect to two or more fluorescing components.

Another aspect of the invention is a device for detecting energy emanating from each one of a plurality of particles moving serially along an aerosol path as the particles move past a predetermined location along the path. The device includes an ellipsoidal reflector disposed with respect to the predetermined path to position a first one of its foci at the selected location. A radiant energy detector is positioned at the other one of the foci.

According to one approach, the device further includes a coherent energy source or causing a beam of coherent energy to intersect the path at the selected location. In this case the energy emanating from each of the particles consists essentially of scattered coherent energy, and the detector comprises an avalanche photodetector. In another approach, the device includes an excitation source for causing excitation energy to intersect the path at the selected location to cause the particles to emit responsive signals. In this case, energy emanating from the particles consists essentially of the responsive signals, and the preferred detector is a photomultiplier tube. Further according to the present invention, these approaches can be combined in a single device with two ellipsoidal reflectors, one for sensing coherent energy scattered from a first location along the path and the other for sensing fluorescent signals emitted by particles at a second location downstream from the first location.

Thus in accordance with the present invention, information about individual particle size and composition is generated in real time and with a high degree of sensitivity, despite using relatively low energy continuous wave lasers for measuring aerodynamic size, and a low energy pulsed laser for providing excitation energy. Time-of-flight measurements are used to rapidly generate aerodynamic size information and timing information used to pulse the source of excitation energy. Improvements in sensitivity are achieved by employing energy concentration structures such as ellipsoidal mirrors to augment the emitted energy provided to photomultiplier tubes or other detectors. The lower laser energy levels and increased detection sensitivity combine to provide a less costly and more reliable instrument for generating real time particle size and composition information.

IN THE DRAWINGS

For a further understanding of the above and other features and advantages, reference is made to the following detailed description and to the drawings, in which.

DETAILED DESCRIPTION OF THE PREFERRED EMBODIMENT

Figure 1:
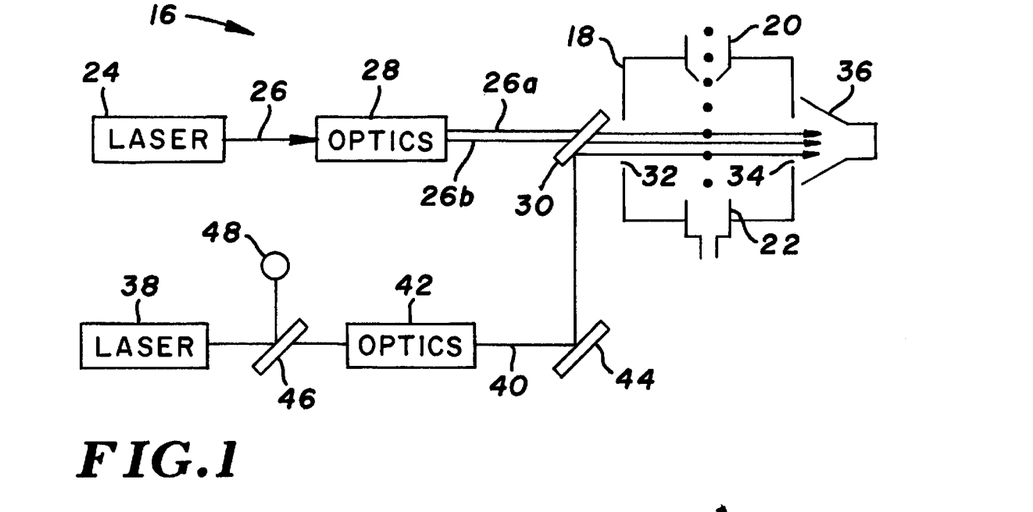
FIG. 1 is a schematic view of a system for characterizing aerosol particles as to size and the presence of a biological material or other fluorescing component, constructed according to the present invention.

Turning now to the drawings, there is shown in FIG. 1 an electrode-optical system 16 for characterizing particles in a gas stream. The system incorporates two interacting subsystems: a gas flow system for generating a flow or stream of a gas, and an optical system for viewing the gas stream and characterizing particles carried in the gas stream. Each of the particles is characterized individually, in terms of its size, and the presence or absence of detectable fluorescent constituents. As indicated above, certain biological components are known to emit fluorescent signals when irradiated with excitation energy, e.g., ultra-violet light. Accordingly, system 16 is capable of examining aerosol particles for the presence of biological components and other fluorescent materials.

Considering first the gas flow system, gas (usually air) containing particles is drawn into a chamber 18 through a nozzle assembly 20 built into a top wall of the chamber. An exit conduit 22 extends upwardly through a bottom wall of the chamber. Gas is drawn out of the chamber through the exit conduit, to maintain a reduced pressure inside the chamber and thus draw a continuous flow of the gas and particles through the nozzle assembly into the chamber. For a more detailed explanation of the gas flow system, reference is made to the aforementioned U.S. Pat. No. 5,561,515.

The optical system includes a radiant energy source, in this case a diode laser 24 operated in the CW (continuous wave) mode, emitting a beam 26 in the visible range, more particularly red light having a wavelength of about 680 nm. The laser beam is directed through a series of beam sizing and shaping components, indicated collectively in the figure as beam-shaping optics 28. The optics include a beam-dividing component, so that the beam emerges from optics 28 as a pair of parallel, slightly overlapping beams 26*a* and 26*b*. These beams proceed to a dichroic separator 30 that transmits the beams into chamber 18 through a window 32 to intersect the particle stream. Beams 26*a* and 26*b* are focused along the region where they intersect the particle stream. Beyond the particle stream, the beams proceed out of the chamber through an aperture 34, into a light stop or trap 36 designed to ensure that only light scattered or emitted by the particles is sensed. For a more detailed description of the optics, including reference to specific beam-shaping components, reference is again made to U.S. Pat. No. 5,561,515.

In system 16, the optical subsystem further includes a diode pumped Nd: YAG pulsed UV laser 38 for generating a UV (ultra violet) beam 40 having a wavelength in the range of 349–355 nm. Beam-shaping optics 42 shape the UV beam in the matter discussed above with beam 26. Beam 40, however, is provided to a reflector 44 as a single beam, proceeding upwardly to dichroic separator 30. Separator 30 reflects frequencies in the UV range. Accordingly, beam 40 is reflected rather than transmitted, and proceeds into chamber 18 parallel to and transversely spaced apart from beams 26*a* and 26*b*, below the red beams as shown in FIG. 1. Preferably, beam 40 is offset from the other beams by a distance of about 300 microns. UV beam 40 intersects the particle path downstream of beams 26*a* and 26*b*, then proceeds out of the chamber into light stop 36. As it proceeds toward the beam-shaping optics, UV beam 40 passes through a substantially transparent window 46 set at a 45-degree angle relative to the beam. Window 46 reflects a small portion of the UV radiation to a photodetector 48 used to monitor the UV pulse energy.

FIG. 2 shows a portion of system 16, in particular the region proximate the intersections of the beams and particle stream, as viewed looking along the beam axes in the direction away from light stop 36. This view illustrates the flattened or elliptical profiles of beams 26*a*, 26*b* and 40. As noted in the aforementioned U.S. Pat. No. 5,561,515, the elliptical profiles ensure more consistency in the amount of light scattered by a given particle, regardless of whether it is precisely centered within the beam or slightly off-center. This figure further illustrates the slight overlap of beams 26*a* and 26*b*, which is used in connection with appropriate signal processing to reject erroneous readings based on single-trigger or coincidence events.

Positioned on opposite sides of the beams and particle stream, are two ellipsoidal reflectors or mirrors, indicated respectively at 50 and 52. An opening 54 built into reflector 50 allows radiant energy to proceed beyond reflector 50 to a fluorescence detector, in particular a photomultiplier tube 56. Light received by photomultiplier tube 56 travels through optical filters 58 and 60. Similarly, an opening 62 in reflector 52 allows energy to reach an avalanche photodetector 64 through an optical filter 66. Photodetector 64 senses energy at the red (680 nm) wavelengths, scattered by the particles.

In FIG. 3, the region proximate the beam/particle stream intersections is shown as seen from above, looking along the particle stream. Again, ellipsoidal mirrors 50 and 52 are shown on opposite sides of the beams, which in this view appear as a single beam.

Detectors 56 and 64 each generate electrical (voltage) outputs that vary in proportion to the amplitude of received energy. The detector electrical signal outputs are shown at 68 and 70, respectively. Optical filter 66 blocks the shorter wavelengths UV excitation energy and the responsive fluorescence emissions of the particles, to ensure that avalanche photodetector 64 receives only scattered red light. Similarly, optical filter 58 blocks the excitation wavelength and optical filter 60 blocks the red wavelength, to ensure that photomultiplier tube 56 receives only the fluorescence signals emitted by the particles.

Figure 2:
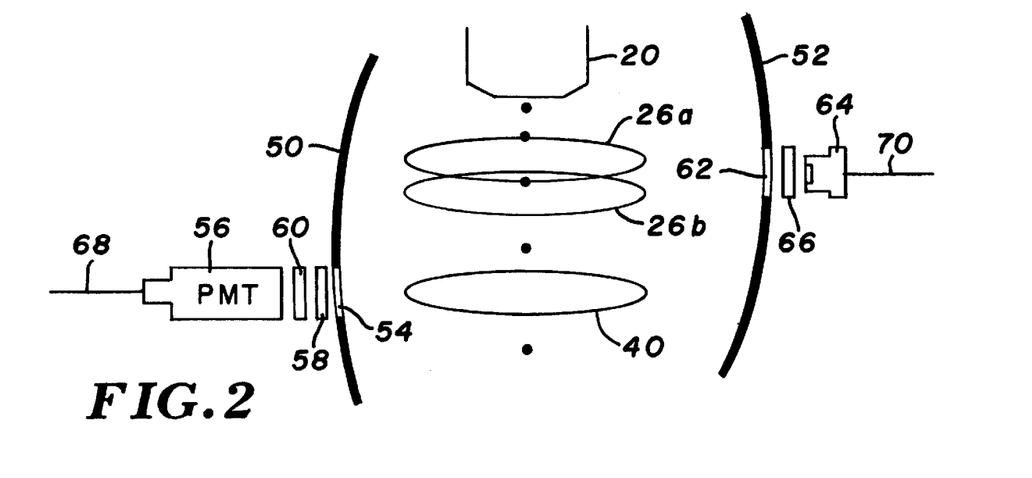
FIG. 2 is a schematic view of a portion of the system where several laser beams intersect a particle stream, viewed in the direction of the beam axes.
Figure 3:
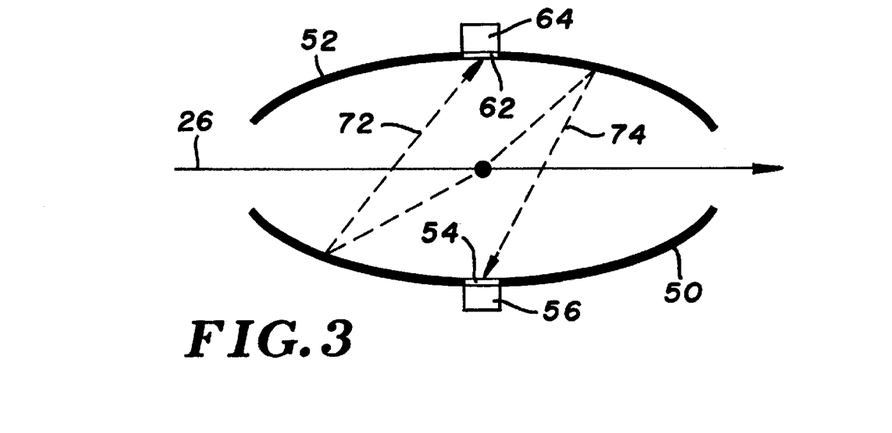
FIG. 3 is a schematic view of substantially the same part of the system as shown in FIG. 2, viewed in the direction of particle stream movement.

As seen in FIGS. 2 and 3, ellipsoidal mirrors 50 and 52 act as energy collectors or concentrators to enhance the sensitivity of the instrument for detecting scattered and emitted energy.

In particular as to red wavelengths, mirror 50 is positioned to locate one of its foci where overlapping beams 26a and 26b intersect the particle stream. The other of the foci is positioned at the entry to avalanche photodetector 64. Accordingly, any scattered energy that reaches mirror 50, regardless of the particular location along the mirror, is reflected toward the other focus of the ellipse, i.e., toward the avalanche photodetector. Broken line 72 in FIG. 3 illustrates one example.

With respect to fluorescence emissions, mirror 52 is positioned with one of its foci at the intersection of beam 40 and the particle stream, and with the other one of its foci at the entry to photomultiplier tube 56. A particle when irradiated by UV beam 40, emits fluorescent energy, e.g., at a wavelength longer than that of beam 40, for example within the range of 400–580 nm. As indicated by a broken line 74 in FIG. 3, emitted fluorescence that encounters the ellipsoidal reflective surface of mirror 50, having emanated from one of the focal points, is reflected to the other focal point, i.e., through opening 62 to the photomultiplier tube.

Accordingly, each of ellipsoidal mirrors 50 and 52 collects and concentrates energy emanating from the particles, and reflects the energy to its associated detector, with optical filters ensuring that only the appropriate wavelength is detected.

Figure 4:
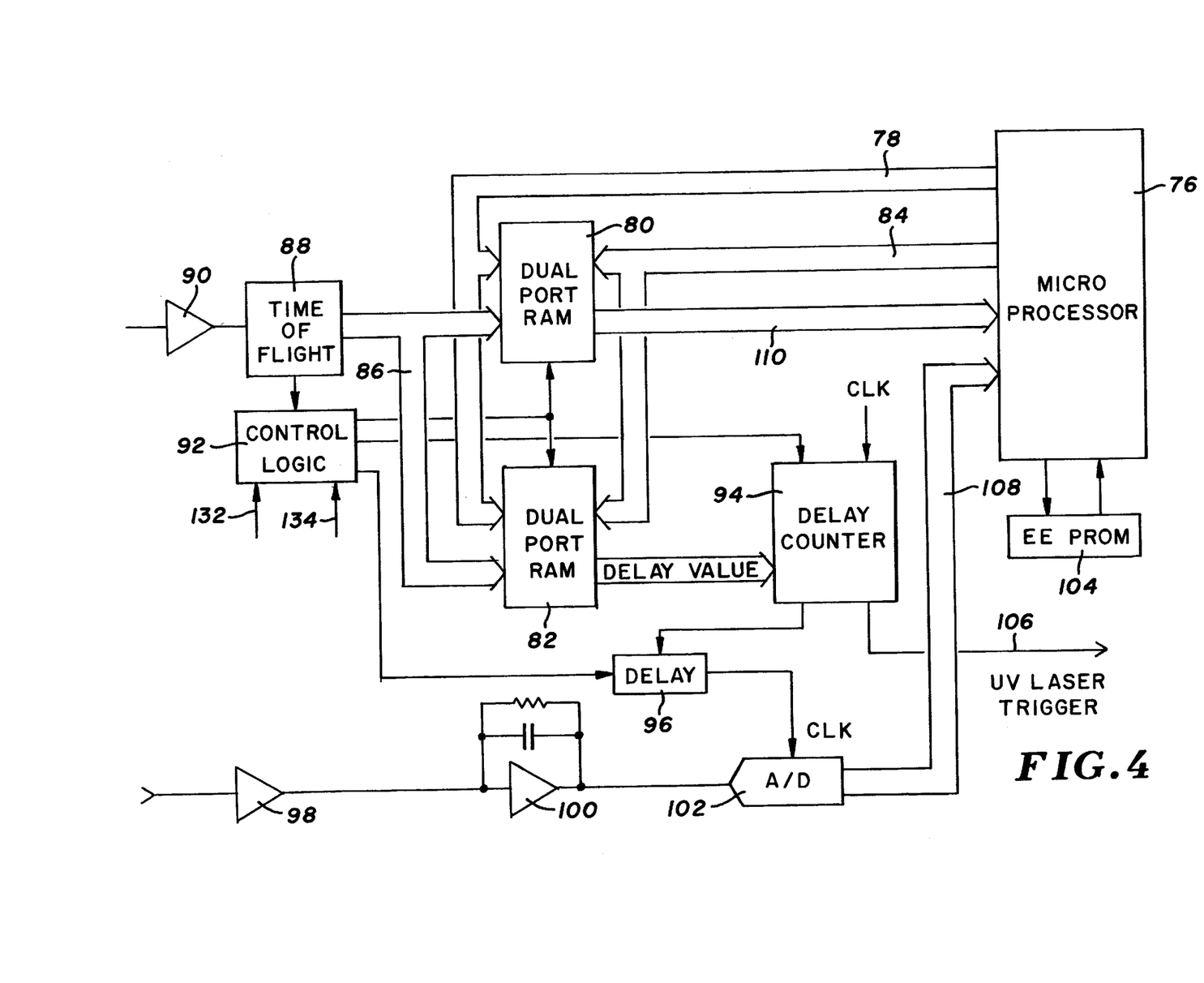
FIG. 4 is a circuit diagram illustrating operation of the system.

FIG. 4 is a block diagram illustrating measurement and control functions within system 16. The measuring and control circuitry includes a microprocessor 76 and a nonvolatile programmable memory (EEPROM) 104 coupled to the microprocessor. Microprocessor 76 uses a channel 78 to provide address data to a pair of memories 80 and 82 for storing look-up table information. Each of the memories is a dual port RAM (random access memory). Through another channel 84, the microprocessor loads look-up data (as opposed to the addresses for writing the look-up data). The other input 86 to memories 80 and 82 provides digital time-of-flight values, i.e., digital words representing measured particle transit times. The transit times, which represent the time for the particles to travel from the center beam 26a to the center beam 26b, are provided by a transit time A/D (analog to digital) converter 88 that converts voltage levels from an amplifier 90 into the corresponding digital words. The A/D converter also provides an input to a control logic circuit 92 coupled to memories 80 and 82. The control logic also is coupled to a laser trigger delay counter 94 and an auxiliary delay counter 96. An amplifier 98 receives an input signal from photomulitiplier tube 56 that varies with the level of detected fluorescence. The output of amplifier 98 is provided to an integrator 100, which in turn provides its output to an A/D converter 102 that provides the corresponding digital fluorescence values to microprocessor 76.

The measurement and UV laser control functions of the circuitry in FIG. 4 depend on transit time information, which is generated by amplifier 90 based on a ramped voltage or other appropriate analog time-of-flight indicator. A/D converter 88 converts the amplifier output into digital representations of the respective transit times, providing them to memories 80 and 82.

Figure 5:
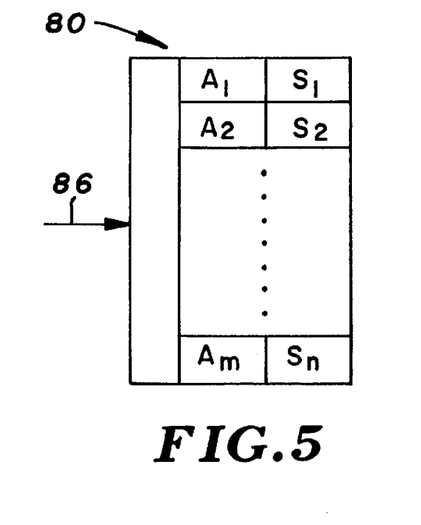
FIG. 5 is an enlarged view of a memory component of the circuit in FIG. 4, used to generate aerodynamic size values.

As seen in FIG. 5, memory 80 contains multiple addresses $A_1$ through $A_m$, each corresponding to a different transit time. Memory 80 also contains multiple aerodynamic size values $S_1$ through $S_n$, each size paired with one or more (usually several) of the addresses. For example, 50 sizes might be paired with 1,000 addresses. Together, the addresses and size values provide calibration information that usually is stored in EEPROM 104, and loaded by the microprocessor into memory 80 for use during operation of the system. In operation, each incoming digital transit time is matched to its corresponding address, whereupon memory 80 provides the corresponding aerodynamic size value to the microprocessor.

Figure 6:
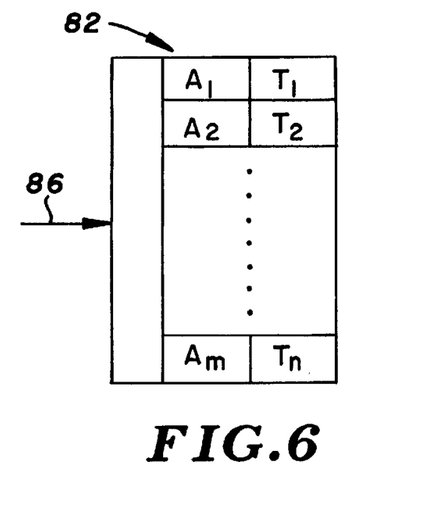
FIG. 6 is an enlarged view of a memory component of the logic circuit, used to generate time delay counts.

Memory 82 is similarly configured with multiple delay time values $T_1$ through $T_n$ paired with one or more addresses. FIG. 6 illustrates the multiple transit time addresses and corresponding multiple time delay values stored in memory 82. Responsive to receiving a given transit time, memory 82 matches the given time to the corresponding address and provides the appropriate delay time value to counter 94. Counter 94 decrements the received count, and upon reaching 0, provides a triggering command at 106 to UV laser 38.

The particles are accelerated as they travel through the region illustrated in FIGS. 2 and 3. Accordingly, the required delay time values do not exhibit a straight-line proportionality to the measured transit times, and the relationship between the transit times and delay time values reflects a more complex function. Accordingly, the system is calibrated. First, a series of different monosized distributions of particles containing fluorescent material, each of a known average size, is drawn through chamber 18. Meanwhile, the UV laser trigger delay counter is swept through a range of delay times during each distribution. About five to ten distributions are run, with different sizes extending over an appropriate range, e.g., 0.5 to 15 micrometers. For each size, the maximum average fluorescence measurement corresponds to the optimal delay. Then, the resulting pairs of optimal delay times and sizes are matched to an appropriate mathematical function that provides a close fit to the actual relationship. e.g.:

Delay count=A+B *exp (transit time/C), where A, B and C are constants of the calibration function. The constants thus derived are used to complete the calibration data by providing intermediate time delay values for sizes (transit times) not tested. Again, the data are stored in EEPROM memory 104 for the long term, and loaded into memory 82 by the microprocessor as system 16 is activated for use.

For each fluorescence measurement, the acceptance of input from photomultiplier tube 56 is timed to coincide with the firing of UV laser 38 and the resulting fluorescence emission from the particle. To this end, counter 94 provides its output to auxiliary counter 96, which accounts for the characteristic delay between the instant that UV laser 38 receives trigger input 106 and the time it actually fires the UV pulse. Counter 96 provides an input to A/D converter 102, to enable a sampling of the integrated photomultiplier output, an analog value that is converted to a digital value provided to microprocessor 76 over a channel 108. Meanwhile, memory 80 provides aerodynamic size information to the microprocessor via a channel 110.

As an alternative to additional counter 96, a photodetector can be provided to sense the firing of UV laser 38 directly, and in response enable A/D converter 102. In either case, measured fluorescence emissions can be corrected to account for variations in the power of UV laser 38, as measured by photodetector 48.

Figure 7:
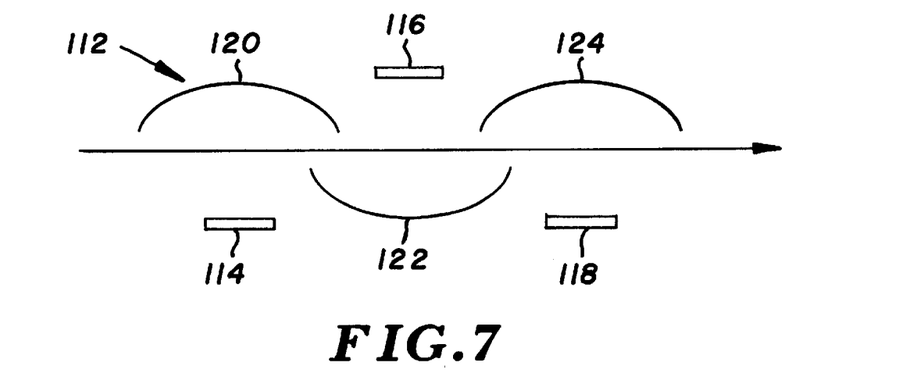
FIG. 7 is a partial view of an alternative embodiment system for recognizing several different fluorescing constituents.

FIG. 7 illustrates a detector array 112 for sensing fluorescence according to an alternative embodiment of the invention. In particular, a series of photomultiplier tubes 114, 116 and 118 are arranged along the particle path, and are sensitive to fluorescence over different ranges of wavelengths, e.g., 450–500 nm; 475–525 nm; and 500–550 nm. Ellipsoidal reflectors 120, 122 and 124 cooperate with detectors 114, 116 and 118, respectively, concentrating emitted energy as previously described.

Figure 8:
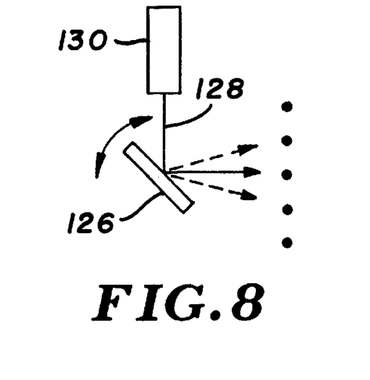
FIG. 8 illustrates another alternative embodiment system with a variably positionable UV energy beam.

FIG. 8 illustrates an irradiation arrangement of a further alternative embodiment, namely a mirror 126 movable to guide a UV beam 128 from a laser 130 over a range of locations along a particle stream. This approach enables the use of a single rather than variable time delay for UV laser firing, yet can accommodate a variation in particle velocities and accelerations.

Figure 9:
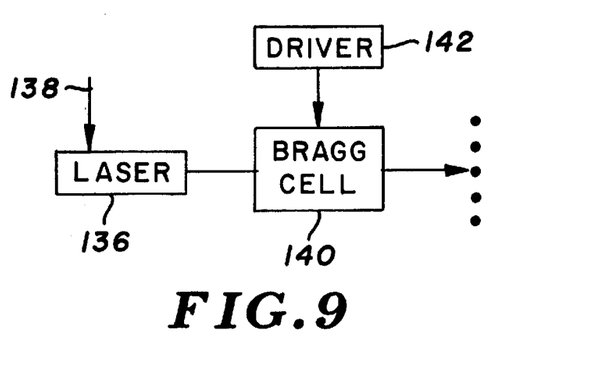
FIG. 9 illustrates part of a further alternative system in which the UV laser is selectively controlled as to amplitude or frequency.

According to a further embodiment of the invention, control circuit 92 can be adapted to govern the firing of UV laser 38, the sensing of fluorescence, or both, according to predetermined settings. For example, maximum and minimum inputs 132 and 134 can be used to limit UV irradiation to particles within a selected range of sizes (transit times), or to particles having at least (or at most) a given size. The ability to selectively trigger irradiation only in connection with selected sizes can be used, for example, to detect bacteria in clusters, as opposed to individual specimens with diameters less than 0.9 microns, by triggering UV laser 38 only for measured sizes at or above 0.9 microns.

According to another embodiment system, the intensity of the UV pulse, or alternatively its wavelength, is controlled based on transit time measurements. In general, larger particles produce brighter fluorescence signals, permitting a lower intensity UV irradiation. A power-controlling input to a UV laser 136 is indicated at 138.

In connection with controlling the wavelength, the output of laser 136 is directed through a Bragg cell 140 (acoustical-optic modulator), or an electro-optic modulator such as a Pockels cell or a Kerr cell. A driver 142, coupled to the Bragg cell, is used to selectively alter the frequency.

Thus, in accordance with the present invention, rapid and reliable real time information is generated, with respect to the individual particles of a particle stream. A high-sensitivity detection arrangement permits the use of low energy continuous wave lasers for aerodynamic size measurements, as well as low energy pulsed UV lasers for irradiating the particles to stimulate fluorescent emissions. Transit time measurements are used both for providing aerodynamic sizes and for determining, in connection with each particle, the appropriate timing of UV laser irradiation.

What is claimed is:

1. A process for characterizing particles in aerosols, including:
   causing an aerosol to move along a predetermined path as a stream of successive particles detectable individually at least at first and second different locations along the path;
   accelerating the aerosol along a predetermined segment of the path that includes the first and second locations;
   measuring respective transit times for the particles, with the transit time in each case indicating the time for the respective particle to travel from the first location to the second location;
   intermittently causing excitation energy to intersect the path at a third location downstream of the first and second locations, to individually irradiate each of the particles with the excitation energy, wherein the excitation energy has a frequency within a range selected to trigger a responsive emission by a predetermined constituent; and
   responsive to each episode of said irradiating, sensing for the presence of a responsive emission from the particle to facilitate determining whether that particle contains the predetermined constituent.

2. The process of claim 1 wherein:

said measuring of each particle includes causing first and second coherent energy beams to intersect the path at the first and second locations, respectively, and detecting coherent energy scattered by the particle as it intersects each of the beams.

3. The process of claim 2 further including:

measuring an intensity of the coherent energy scattered by the particle.

4. The process of claim 1 further including:

providing a calibrated look-up table containing a plurality of aerodynamic size values individually associated with a plurality of transit times, and providing each of the transit times to the look-up table to generate the associated aerodynamic size.

5. The process of claim 1 wherein:

said intermittently causing excitation energy to intersect the path comprises causing a pulsed laser to deliver an excitation beam in response to sensing coherent energy scattered by the particle as it passes at least one of the first and second locations.

6. The process of claim 5 wherein:

said intermittently causing excitation energy to intersect the path further includes using the transit time for a given particle to determine the time for generating the excitation energy to irradiate that particle at the third location.

7. The process of claim 6 wherein:

the time for generating the excitation beam is determined based on a calibration function:

Delay count=A+B *exp (transit time/C), where A, B and C are constants of the calibration function empirically derived from calibration data.

8. The process of claim 6 wherein:

the determining of the time to generate the excitation energy includes providing a calibrated look-up table containing a plurality of time delay values associated individually with each one of a plurality of transit times, and providing the transit time of a given particle to the look-up table to generate the associated time delay value, then generating the excitation energy in accordance with the time delay value.

9. The process of claim 1 wherein:

said sensing for a responsive emission comprises positioning a fluorescence detector proximate the third location.

10. The process of claim 9 further including:

operatively coupling an energy concentrator to the fluorescence detector to enhance detection sensitivity.

11. The process of claim 10 wherein:

the energy concentrator comprises an ellipsoidal reflector, and the operative coupling comprises positioning the reflector with one of its foci at the third location, and positioning the fluorescence detector at the other one of the foci.

12. A particle characterizing system, including:

a flow generating device for moving an aerosol along a designated path with particles of the aerosol in series, and accelerating the aerosol along a selected segment of the path including first and second different locations along the path;

a measuring device for measuring transit times indicating respectively for each one of the particles a time for the particle to travel from the first location to the second location;

an excitation component for generating excitation energy at a frequency within a predetermined excitation frequency range selected to cause an emission by a particle in response to irradiation by the excitation energy, and for causing the excitation energy to intersect the path at a third location downstream of the first and second locations;

a timing component for causing the excitation component to generate the excitation energy intermittently as the different ones of the particles travel past the third location, thereby to irradiate each of the particles with the excitation energy; and a sensing component adapted to detect any emission by the particle responsive to the irradiation.

13. The system of claim 12 wherein:

the measuring device comprises a first laser beam intersecting the path at the first location, a second laser beam intersecting the path at the second location, and a detection means for detecting laser energy scattered by each one of the particles as it moves past the first and second locations.

14. The system of claim 13 further including:

a means for measuring the magnitude of the scattered coherent energy.

15. The system of claim 12 further including:

a calibrated look-up table adapted to store multiple aerodynamic size values and multiple transit times, each of the aerodynamic size values associated individually with one of the transit times.

16. The system of claim 12 wherein:

the excitation component comprises a pulsed UV laser.

17. The system of claim 16 wherein:

the UV laser generates coherent energy having a wavelength in the range of about 349 nm to about 355 nm.

18. The system of claim 17 further including:

a table for storing multiple time delay values and multiple transit times, each of the time delay values uniquely associated with one of the transit times, the table being adapted to generate an associated one of the time delay values responsive to receiving one of the transit times.

19. The system of claim 12 wherein:

the sensing component comprises a photomultiplier tube disposed near the third location.

20. The system of claim 19 further including:

an energy concentrator operatively coupled to the photomultiplier tube.

21. The system of claim 20 wherein:

the energy concentrator comprises an ellipsoidal reflector disposed to place one of its foci at the third location, and wherein the photomultiplier tube is positioned at the other one of the foci of the ellipsoidal reflector.

22. A device for detecting energy emanating from each one of a plurality of particles moving serially along a path as the particles move past a location along the path, including:

an energy source for causing a first beam of coherent energy and a second beam of coherent energy to intersect a predetermined particle path at respective first and second proximate but different locations;

an ellipsoidal reflector disposed with respect to the predetermined path to position a first one of its foci along the predetermined path at a selected location proximate the first and second locations; and a radiant energy detector positioned at a second one of the foci.

23. The device of claim 22 wherein:

the selected location is between the first and second locations, and the energy emanating from each of the particles consists essentially of scattered coherent energy.

24. The device of claim 23 wherein:

the radiant energy detector comprises an avalanche photodetector.

25. The device of claim 22 further including:

an excitation source for causing excitation energy to intersect the path to cause the particles to emit responsive signals.

26. The device of claim 25 further including:

a photomultiplier tube for sensing the responsive signals.

27. A device for studying aerosols with particles traveling serially along a predetermined path, including:

a first energy source for causing first and second energy beams to intersect an aerosol path at first and second proximate but different locations;

a second energy source for causing a beam of excitation energy to intersect the path at a third location downstream of the first and second locations;

a first reflector positioned with respect to the path to receive light emanating from the first and second locations, and shaped to direct the received light toward a first destination;

a second reflector disposed with respect to the path to receive light emanating from the third location, and shaped to direct the received light toward a second destination;

a first energy detector disposed at the first destination; and a second energy detector positioned at the second destination.

28. The system of claim 12 wherein:

the sensing component comprises a plurality of detectors sensitive to energy at different ranges of frequencies, to facilitate determining the presence of a plurality of different energy emitting components in each of the particles.

29. The system of claim 12 further including:

an excitation controlling means for storing either a single selected transit time, or a pair of transit times to select a range of transit times having upper and lower limits corresponding to the selected transit times; and a controller selectively controlling the timing component and the excitation component to generate the excitation energy only in response to measured transit times on a selected side of the threshold, or within the selected range.

30. The system of claim 12 further including:

a steering means operably associated with the excitation component adjustable to cause the excitation energy to intersect the path over a range of locations; and wherein the timing component, responsive to the respective transit times, positionally adjusts the excitation component to vary the location at which the excitation energy intersects the path in accordance with transit times.

31. The system of claim 12 further including:

a size indicating component that determines an amplitude value associated with each of the transit times, said amplitude value being provided to the excitation component to control an amplitude at which the excitation energy is generated.

32. The process of claim 1 further including:

determining an aerodynamic size of each of the particles, based on its transit time.

33. The process of claim 1 wherein:

the predetermined constituent is a fluorescent component, and the excitation frequency is selected for its capacity to induce fluorescence.

34. The system of claim 12 further including:

a size indicating component for determining an aerodynamic size of each of the particles based on the transit time associated with that particle.

35. The system of claim 12 wherein:

the predetermined constituent is fluorescent, and the excitation energy has a frequency within a range selected to trigger fluorescence.

36. The system of claim 35 wherein:

the predetermined constituent is a biological component, and the excitation energy frequency is selected to induce a fluorescent emission from the biological component.

37. The process of claim 1 wherein:

the predetermined constituent is a biological component, and the step of intermittently causing excitation energy to intercept the path includes irradiating each of the particles with excitation energy at a frequency selected to induce a fluorescent emission by the biological component.

38. The device of claim 27 wherein:

the first reflector is ellipsoidal, and further is positioned with a first one of its foci proximate the first and second locations and with a second one of its foci proximate the first destination.

39. The device of claim 27 wherein:

The second reflector is ellipsoidal, and further is position with a first one of its foci proximate the third location and with a second one of its foci proximate the second destination.

40. The device of claim 27 wherein:

said first energy source is adapted to provide the first and second energy beams in a continuous wave mode, and said second energy source is adapted to provide the beam of excitation energy in a pulsed mode.

* * * * *